United States Patent
Quinn

(10) Patent No.: US 7,048,722 B2
(45) Date of Patent: May 23, 2006

(54) CATHETER

(75) Inventor: David G. Quinn, Grayslake, IL (US)

(73) Assignee: Radius International Limited Partnership, Grayslake, IL (US)

(*) Notice: Subject to any disclaimer, the term of this patent is extended or adjusted under 35 U.S.C. 154(b) by 0 days.

(21) Appl. No.: 10/295,097

(22) Filed: Nov. 15, 2002

(65) Prior Publication Data
US 2003/0097099 A1    May 22, 2003

Related U.S. Application Data

(60) Provisional application No. 60/332,678, filed on Nov. 16, 2001.

(51) Int. Cl.
*A61M 25/00* (2006.01)
(52) U.S. Cl. .................. 604/270; 604/523
(58) Field of Classification Search ........... 604/264, 604/272, 523, 280–2, 39
See application file for complete search history.

(56) References Cited

U.S. PATENT DOCUMENTS

| | | |
|---|---|---|
| 1,879,249 A | 9/1932 | Honsaker |
| 2,116,083 A | 5/1938 | Rüsch |
| 3,384,089 A | 5/1968 | Shriner |
| 3,547,126 A | 12/1970 | Birtwell |

(Continued)

FOREIGN PATENT DOCUMENTS

DE    43 20 186 C2    12/1994

OTHER PUBLICATIONS

Moss, Gerals, PhD, MD, FACS, "Incomparable Moss® Tubes . . . (but compare with other feeding-decompression tubes anyway.)", pp. 1-2.

*Primary Examiner*—Cris Rodriguez
(74) *Attorney, Agent, or Firm*—Brinks Hofer Gilson & Lione

(57) ABSTRACT

An enteral feeding catheter that provides access to both the stomach and the jejunum for feeding, aspiration and decompression. The catheter includes a dual lumen "D" tube that joins to an external "Y" connector at the proximal end of the tube. The connector serves both lumens as a source for fluid or aspiration. The gastric lumen and the jejunal lumen of the "D" tube both connect to a transitional connector bolus in the stomach. The gastric lumen of the "D" tube joins with a lumen in the transitional bolus that communicates with a gastric port. The gastric port is recessed to the level of its full internal lumen, thereby providing maximum protection against occlusion and maximum area for outflow. The "D" jejunal lumen connects in the bolus with a lumen that transitions from a "D" shape to a full circle shape. The latter provides for the attachment of a smaller, round, single lumen tube that extends into the jejunum. At the distal end of the jejunal tube is a bolus containing an improved port that is also recessed to the level of the floor of the internal tube lumen to provide maximum protection against occlusion and maximum area for outflow. Both the gastric port in the transitional bolus and the jejunal port in the tip bolus include a structural arch protruding radially outwardly therefrom. The arch is effective to prevent the body segment of either bolus from bending and restricting the ports. The invention also provides for the insertion of the tube over a guidewire rather than with an internal stylet, as is normally the case with nasally inserted tubes.

23 Claims, 9 Drawing Sheets

U.S. PATENT DOCUMENTS

| | | | |
|---|---|---|---|
| 3,812,860 | A | 5/1974 | Gilbert et al. |
| 4,356,824 | A | 11/1982 | Vazquez |
| 4,419,094 | A | 12/1983 | Patel |
| 4,431,426 | A | 2/1984 | Groshong et al. |
| 4,490,143 | A | 12/1984 | Quinn et al. |
| 4,496,347 | A | 1/1985 | MacLean et al. |
| 4,529,399 | A | 7/1985 | Groshong et al. |
| 4,543,089 | A | 9/1985 | Moss |
| 4,549,879 | A | 10/1985 | Groshong et al. |
| 4,559,046 | A | 12/1985 | Groshong et al. |
| 4,568,329 | A | 2/1986 | Mahurkar |
| 4,576,603 | A | 3/1986 | Moss |
| 4,583,968 | A | 4/1986 | Mahurkar |
| 4,594,074 | A | 6/1986 | Andersen et al. |
| 4,613,323 | A | 9/1986 | Norton et al. |
| 4,623,327 | A | 11/1986 | Mahurkar |
| 4,642,092 | A | 2/1987 | Moss |
| 4,666,433 | A | 5/1987 | Parks |
| 4,668,225 | A | 5/1987 | Russo et al. |
| 4,671,796 | A | 6/1987 | Groshong et al. |
| 4,685,901 | A | 8/1987 | Parks |
| 4,692,141 | A | 9/1987 | Mahurkar |
| 4,701,166 | A | 10/1987 | Groshong et al. |
| 4,769,014 | A | 9/1988 | Russo |
| 4,770,652 | A | 9/1988 | Mahurkar |
| 4,795,430 | A | 1/1989 | Quinn et al. |
| 4,808,155 | A | 2/1989 | Mahurkar |
| 4,834,712 | A | 5/1989 | Quinn et al. |
| 4,842,582 | A | 6/1989 | Mahurkar |
| 4,900,306 | A | 2/1990 | Quinn et al. |
| 4,981,471 | A | 1/1991 | Quinn et al. |
| 5,084,014 | A | 1/1992 | Picha et al. |
| 5,160,342 | A | 11/1992 | Reger et al. |
| 5,178,625 | A | 1/1993 | Groshong |
| 5,197,951 | A | 3/1993 | Mahurkar |
| 5,221,255 | A | 6/1993 | Mahurkar et al. |
| 5,221,256 | A | 6/1993 | Mahurkar |
| 5,242,389 | A | 9/1993 | Schrader et al. |
| 5,269,770 | A | 12/1993 | Conway et al. |
| 5,374,245 | A | 12/1994 | Mahurkar |
| 5,378,230 | A | 1/1995 | Mahurkar |
| 5,451,216 | A | 9/1995 | Quinn |
| 5,486,159 | A | 1/1996 | Mahurkar |
| 5,498,249 | A | 3/1996 | Quinn |
| 5,520,662 | A | 5/1996 | Moss |
| 5,571,093 | A * | 11/1996 | Cruz et al. ............ 604/270 |
| 5,599,322 | A | 2/1997 | Quinn |
| 5,776,111 | A | 7/1998 | Tesio |
| 5,807,339 | A | 9/1998 | Boström et al. |
| 5,810,787 | A | 9/1998 | Quinn |
| 5,902,285 | A | 5/1999 | Kudsk et al. |
| 6,511,474 | B1 | 1/2003 | Andersen |
| 6,702,776 | B1 * | 3/2004 | Quinn ............ 604/43 |

\* cited by examiner

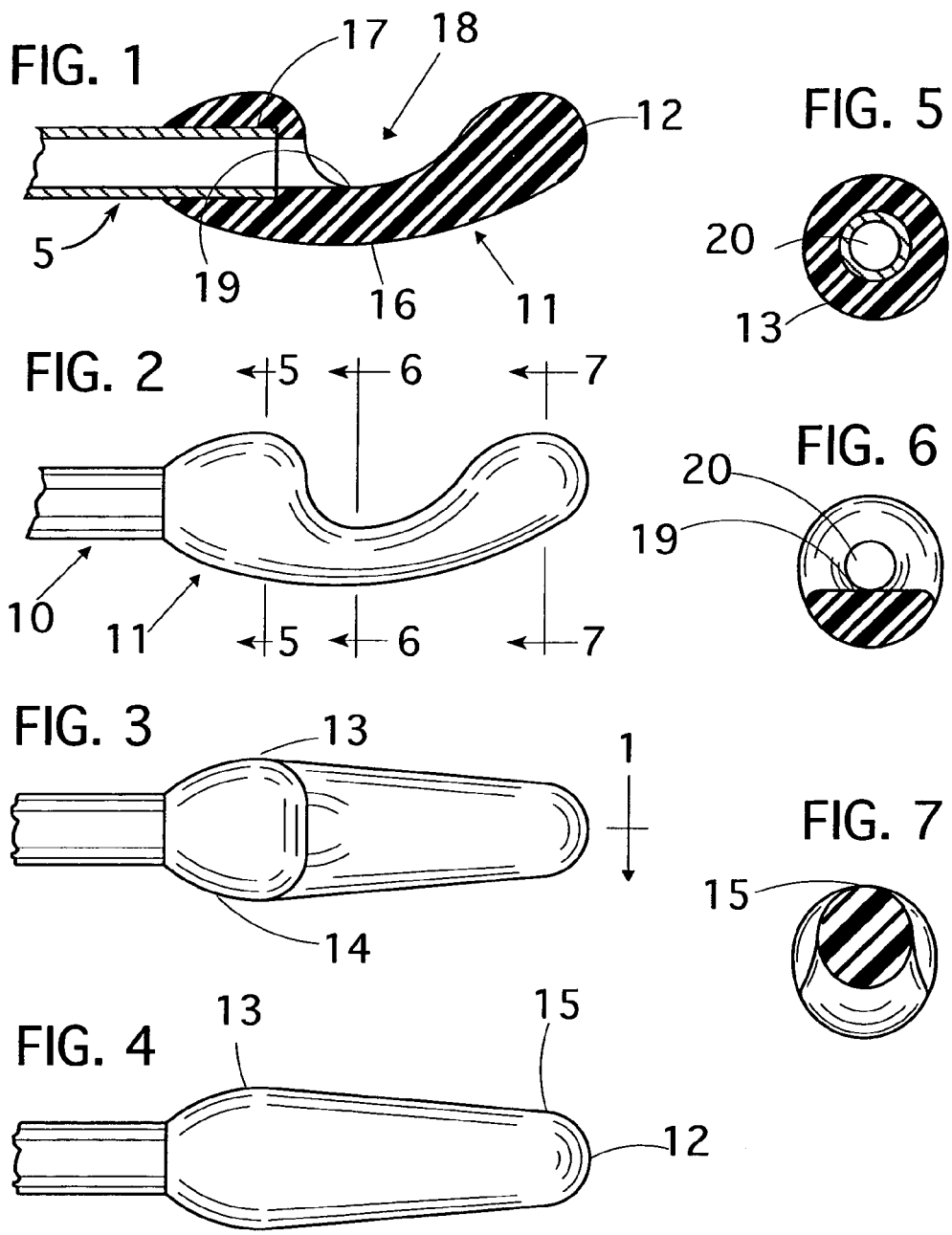

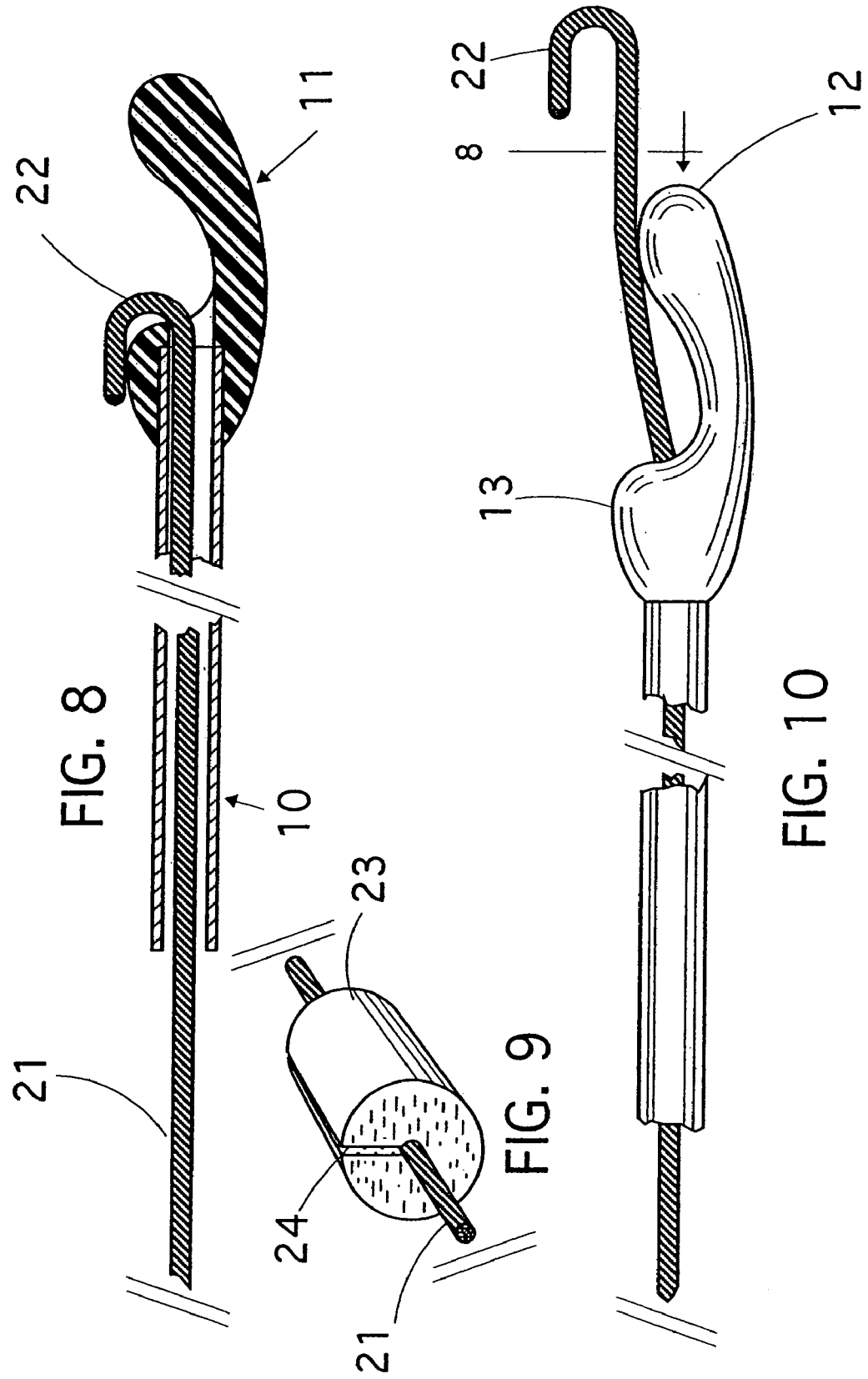

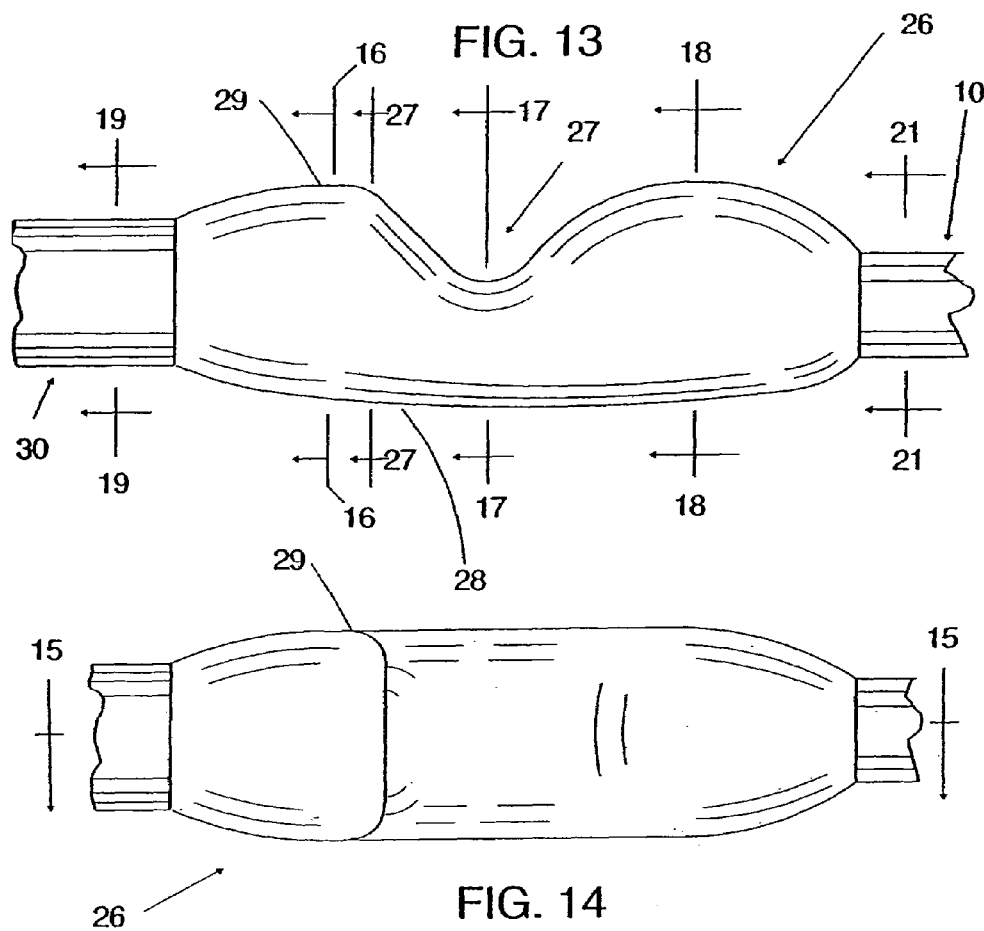
FIG. 13
FIG. 14
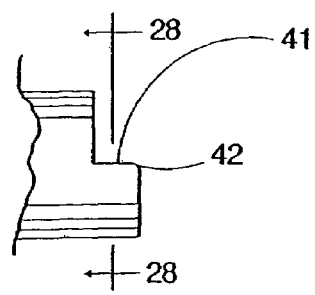
FIG. 26

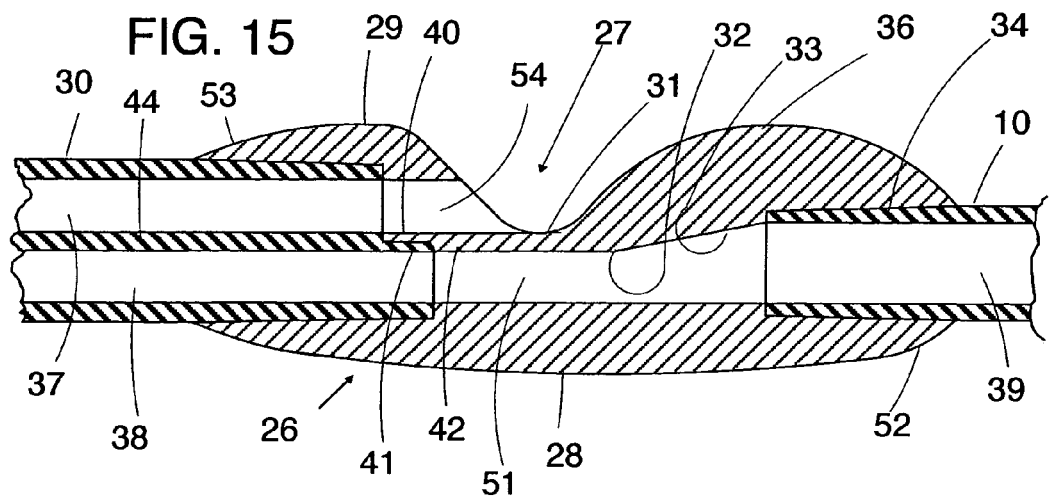
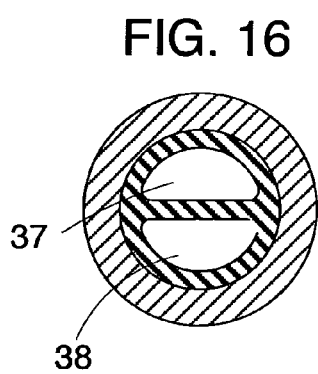
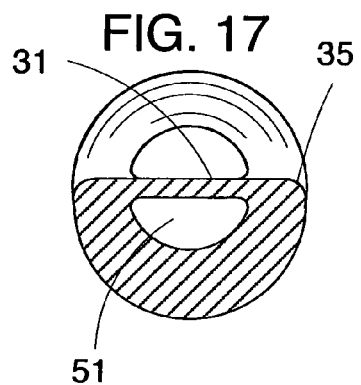
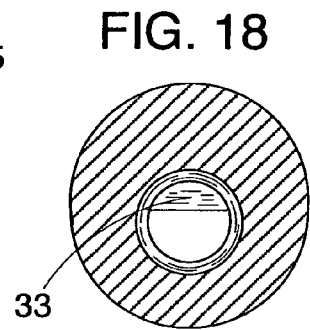
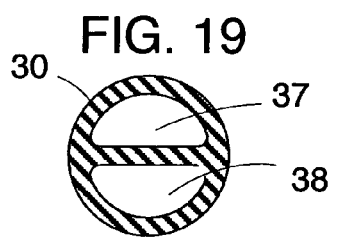
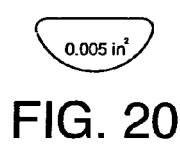
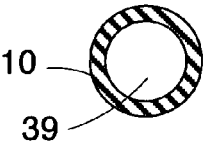
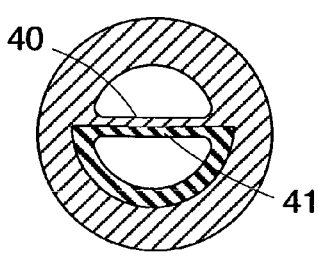
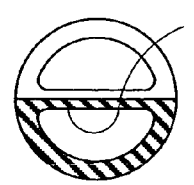
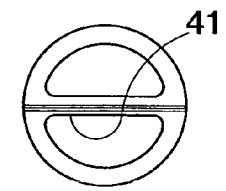

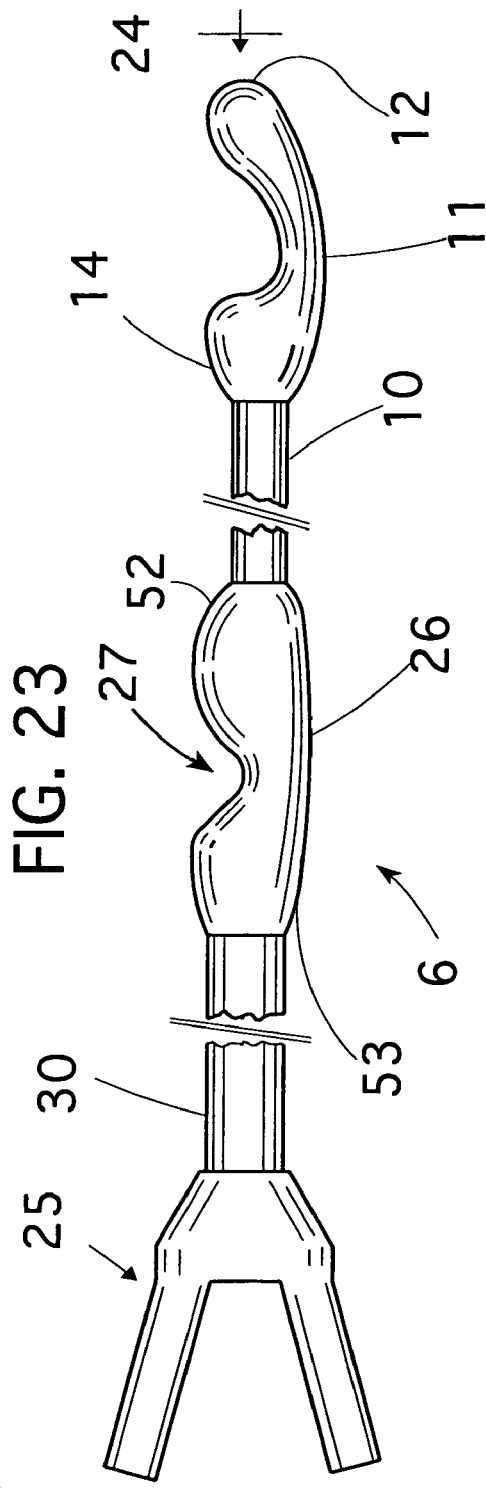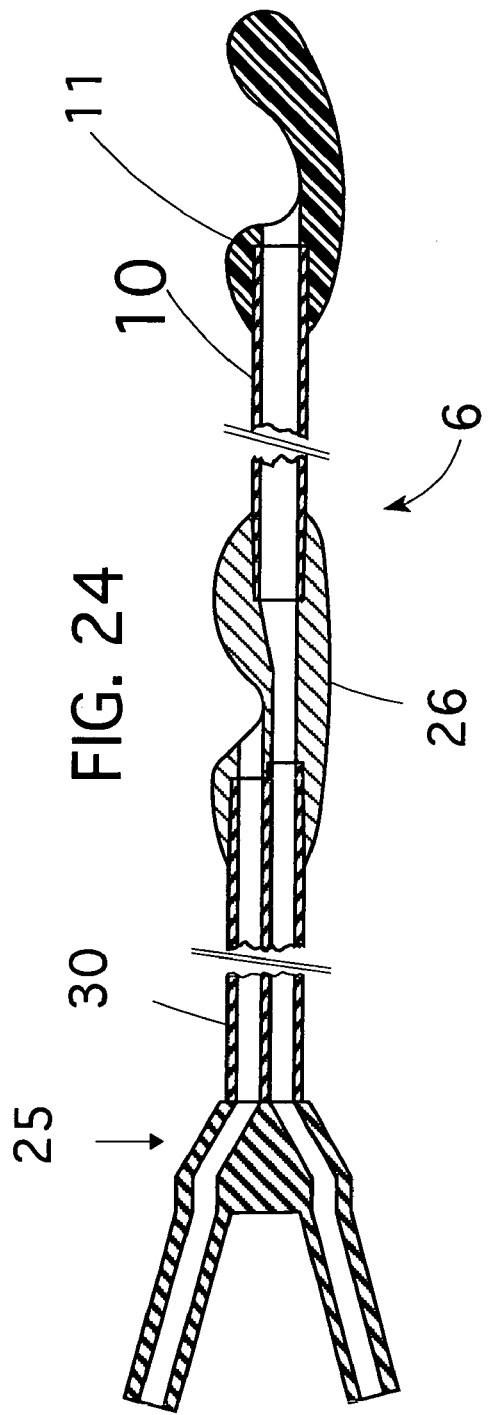

CATHETER

RELATED APPLICATION

This application is based on U.S. Provisional Patent Application Ser. No. 60/332,678, filed Nov. 16, 2001, and claims the priority benefit thereof.

FIELD OF INVENTION

This invention relates generally to catheters for use in administering fluids to body cavities, irrigating the cavities and aspirating them. It relates particularly to catheters and the distal ends thereof which contain the opening(s) for fluid egress or ingress.

BACKGROUND OF THE INVENTION

Prior art catheter and bolus inventions are disclosed in U.S. Pat. No. 4,594,074, U.S. Pat. No. 5,451,216, U.S. Pat. No. 5,599,322 and U.S. Pat. No. 5,810,787. U.S. Pat. No. 4,594,074, for example, addresses catheter bolus construction as it relates to both aspiration and outflow. The side walls of the bolus at the bolus port are recessed to a height of no more than one half of the internal diameter (ID) of the bolus passage. Lowering the walls below this minimum level would result in bending of the tube. Practically speaking, in the preferred embodiment of this particular catheter bolus, the height of the side the walls bracketing the bolus port must actually be at the full height of the bolus passage.

The three other patents referred to describe a catheter which allows the side walls of the bolus to have a height which is less than one half of the outside diameter of the body. This is accomplished by using side walls that have a continuously curving slope and by providing a body segment that includes a structural arch component protruding radially outward therefrom. This design provides a recessed, protected port that is larger than the port in the catheter bolus of U.S. Pat. No. 4,594,074 while still preventing the bolus from kinking and restricting the port.

The tip boluses disclosed in all of these patents are what are referred to as "smooth" boluses. They are glued over the tube. Usually, the socket of the bolus has side walls that are 0.015 inches thick. The tip bolus is slightly larger than the tube, but only as large as is necessary to form the gluing socket. For an example, a 12FR feeding tube has an outside diameter of 0.158 inches. The OD of the 12FR smooth tip bolus is 0.188, or 0.030 larger than the tube so as to incorporate the socket walls. Thus, the bolus thickness OD is increased to slightly more than that of a 14FR tube (0.184 inches). This increase in thickness from tube to bolus is not important in a nasogastric feeding tube because the tube can easily be passed through the nose, and the size of the tube remaining in the nares is the major factor in patient comfort.

Some nasogastric feeding tube designs have tip boluses that are purposefully made much larger than the tubing for operational purposes. These designs are referred to as "large" boluses or "fat" boluses and are designed provide a shape which is ideal for gripping by peristalsis. Fat boluses are commonly attached to 8FR, 10FR and 12FR tubes and have outside diameters of 0.230 inches, which is considerably larger than even the OD of a 12FR tube, for example.

Difficulty of insertion and clogging of the catheter have heretofore restricted the use of gastric/jejunal feeding tubes or catheters. However, it is generally recognized that jejunal placement is preferred over gastric or duodenally placed catheters. Duodenal placement solves some of the problems of pulmonary aspiration, but the incidence of such aspiration is still 20%. Tubes pull out of the duodenum easily and feeding material leaks back into the stomach. In contrast, the jejunum has strong peristalsis resisting pull-out, and the curves leading to it from the stomach also help resist inadvertent removal.

SUMMARY OF THE INVENTION

An object of the invention is to provide a new and improved catheter bolus construction, a construction which allows for the elimination of the bolus sidewalls described in the aforedescribed prior art patents whereby a port is recessed to the level of the full internal diameter of the connecting tube lumen, whether the lumen has a "D" shape or a fully circular shape.

Another object of the invention is to provide an improved nasogastric/jejunal (NGJ) catheter with gastric and jejunal ingress/egress ports that assure against clogging.

Another object of the invention is to use a fat bolus configuration and increase the size of the port by eliminating the walls, while incorporating a radially protruding structural arch component effective to prevent the bolus body from kinking and restricting the port.

Still another object of the invention is to provide for one directional flexing of the bolus forming the jejunal tip, whereby the tube can be inserted over a guidewire rather than with an internal stylet.

Yet another object is to provide a catheter which allows the tube to move over a guidewire, around bends in the intestine, into the jejunum after the guidewire has been inserted past the Ligament of Treitz by fluoroscopy.

Another object is to provide an improved NGJ catheter that can be introduced over a guidewire which is inserted via fluoroscopy.

Still another object is to provide a NGJ catheter that is of the smallest size possible while at the same time providing adequate ingress and egress of fluid from both the stomach and the jejunum.

Still another object is to provide a NGJ catheter that allows for gastric decompression.

Still another object is to provide a NGJ catheter that is simpler and easier to manufacture than those presently in use.

Yet another object of the invention is to provide a method of solvent bonding a dual lumen tube to a transitional bolus so that there is no leakage between the lumens at the junction of the parts.

Still another object of the invention is to provide a method of solvent bonding a triple lumen tube to a transitional bolus so that there is no leakage between the two main lumens and that the third lumen opens to the stomach.

Another object of the invention is to provide an air inlet line in a three lumen tube so that it is adjacent to the suctioning line, thereby being able to balance the atmosphere in the stomach without being isolated from the suction line.

Yet another object of the invention is to protect the adjacent air and suction lines from the stomach wall by positioning them in a recessed port.

Yet another object of the invention is to provide bolus and bolus tip shapes that are identifiable by x-ray.

Yet another objective of the invention is to provide bolus and bolus tip shapes that are identifiable by "feel" by the surgeon during gastric or intestinal surgery.

The foregoing and other objects are realized in accord with the present invention by providing a catheter with a gastric transitional bolus and a jejunal tip bolus for delivering fluids to, or suctioning fluids from, the body cavity of a patient. The catheter includes a dual lumen tube with a conventional, "Y" shaped connector accessing both of the "D" lumens at the proximal end of the tube. The connector is used to connect the catheter to a source of fluid or suction.

The transitional bolus incorporates a gastric port with no side walls. The jejunal port in this bolus has a passage that transitions from "D" shaped to a circular cross-section so that a single lumen, jejunal tube may be attached.

The jejunal tip bolus has a "fat" configuration. The bolus includes a port that has no side walls and provides the maximum in port size to prevent occlusion in either the inflow or aspiration mode. The jejunal tip bolus is tapered from back to front. This configuration allows the entire bolus to flex and facilitates easy insertion over a guidewire.

Three distinct types of gastric/jejunal catheters are disclosed. The first type is a single lumen tube with a non-occluding tip. This tube has all of the characteristics of standard nasogastric feeding tube, except it is longer so that its tip can be placed into the jejunum. This version benefits from the new tip design, as do all the three versions. This tube is recommended for all routine nasogastric/jejunal feeding over gastric or duodenal placement.

The second type of catheter has a dual "D" lumen tube as its initial, approximately 36 inches long gastric section. Both of the "D" lumens attach to a mid-port, 0.230 inches OD bolus at the distal end of the "D" tube. One lumen accesses a gastric port in the mid-port and the other lumen accesses and transitions to an 8FR tube that continues for another approximately 20 inches to rest in the jejunum. This tube provides for jejunal feeding and also allows for the patients stomach to be aspirated and decompressed. Its usage is more limited than the single lumen type. The gastric mid-port design utilizes the recessed port features of the tip.

The third catheter utilizes a three-lumen tube design. Two lumens access ports in the gastric mid-port and the remaining lumen transitions to the 8FR tube that resides in the jejunum. Recent clinical studies show that early post surgical jejunal feeding helps restart peristalsis after gastric/intestinal surgery, reduces infection and promotes healing.

The practice in the United States is to place a "Salem Sump" catheter into most post gastric/intestinal surgery patients who have lost peristalsis. The "Salem Sump" catheter has two lumens. One is connected to suction and constantly evacuates the build-up of gastric fluid in the patient's stomach. The second lumen allows air to enter the stomach so as to balance the negative pressure caused by the constant suction. The patient is fed only with IV solutions from several days to over a week until peristalsis returns. The three-lumen embodiment of the present invention allows enteral feeding to begin in the jejunum while also allowing constant evacuation of the stomach via wall suction. In Europe, post-surgical suction is now either by intermittent syringe aspiration or by gravity. The dual lumen version of the catheter invention can be used instead.

Other commercial gastric/jejunal catheters employ an inefficient, small tube within a larger tube to access both the stomach and the jejunum. Flow through the larger tube is restricted to the space between the OD of the small tube and ID of the larger tube. This configuration results in low flow, clogging and the necessity of a very large FR (French) size outer tube.

BRIEF DESCRIPTION OF DRAWINGS

The invention, including its construction and method of operation, is illustrated more or less diagrammatically in the drawings, in which:

FIG. 1 is a longitudinal sectional view of the jejunal catheter of the invention taken along line 1—1 of FIG. 3, showing the jejunal bolus tip connected to the catheter tube;

FIG. 2 is a side view of the catheter seen in FIG. 3, showing the bolus connected to the catheter tube;

FIG. 3 is a top plan view of the catheter seen in FIG. 2;

FIG. 4 is a bottom plan view of the catheter seen in FIG. 2;

FIG. 5 is a sectional view taken along line 5—5 of FIG. 2;

FIG. 6 is a sectional view taken along line 6—6 of FIG. 2;

FIG. 7 is a sectional view taken along line 7—7 of FIG. 2;

FIG. 8 is a longitudinal sectional view through a jejunal catheter showing a guidewire in place during initial insertion through the nares when the guidewire is used as a stylet;

FIG. 9 is a perspective view of flexible plug used to trap a guidewire in the jejunal "Y" arm of the proximal connector when the jejunal catheter is placed through the nares;

FIG. 10 is an enlarged side view of the jejunal bolus during insertion showing the bolus end bent downwardly as the guidewire is advanced toward the jejunum, after the bolus is in the stomach;

FIG. 13 is a side view of a gastric/jejunal catheter including a gastric transitional bolus, showing the bolus connected to both gastric and the jejunal tubes;

FIG. 14 is top plan view of the catheter and gastric bolus seen in FIG. 13;

FIG. 15 is a sectional view taken along line 15—15 of FIG. 14;

FIG. 16 is a sectional view taken along line 16—16 of FIG. 13;

FIG. 17 is a sectional view taken along line 17—17 of FIG. 13;

FIG. 18 is a sectional view taken along line 18—18 of FIG. 13;

FIG. 19 is a sectional view of a 12FR "D" shaped tube taken along line 19—19 of FIG. 13;

FIG. 20 shows the area in square inches of a lumen of the 12FR "D" shaped lumen seen in FIG. 19;

FIG. 21 is a sectional view taken along line 21—21 of the 8FR jejunal tube in FIG. 13;

FIG. 22 shows the area in square inches of a lumen of the 8FR tube lumen;

FIG. 23 is a side view of the entire gastric/jejunal catheter, including "Y" connector, the transitional gastric bolus and the jejunal bolus;

FIG. 24 is a longitudinal sectional view through the gastric/jejunal catheter of FIG. 23;

FIG. 26 is a side elevational view of the distal end of the gastric lumen seen in FIG. 15;

FIG. 27 is a sectional view taken along line 27—27 of FIG. 13;

FIG. 28 is a sectional view taken along line 28—28 of FIG. 26;

FIG. 29 is an end view of the lumen seen in FIGS. 15 and 26;

DESCRIPTION OF THE PREFERRED EMBODIMENTS

Figure 11:
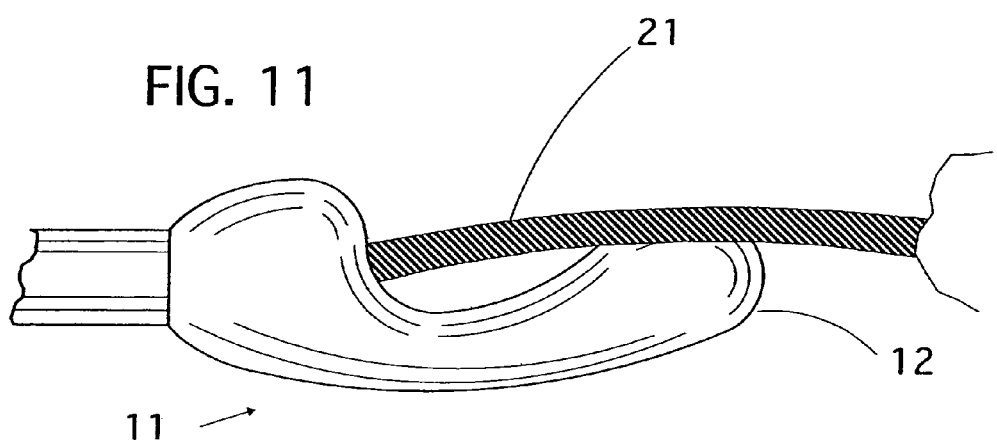
FIG. 11 is an enlarged side view of the jejunal bolus during insertion showing the position of the guidewire when the bolus follows the guidewire around a curve.

"Referring now to the drawings, and particularly to FIGS. 1 through 12, a catheter 5 embodying features of the invention includes an 8FR tube 10 shown seated in a socket 17 which extends 0.185 inches into the connector end 14 of a jejunal tip bolus 11. The OD of the bolus 11 at 13, which is shown in FIG. 5, is 0.230 inches. The OD of the bolus 11 at 15, which is shown in FIG. 7, is 0.152 inches. The bolus 11 is a "fat" bolus."

A struture 16 in the bottom of the bolus forms an are opposite the port 18. The structural arc 16 prevents bending of he bolus toward the port, i.e., kinking, and subsequent occlusion of the port. The structural arc 16 extends 0.016 inches outside the normal maximum bolus OD of 0.230 inches.

As seen in FIG. 3, the bolus 11 tapers from its widest point at 13 to its narrowest point at 15. This taper prevents the bolus tip 12 from bending sideways out of the configuration shown in FIGS. 3 and 4.

Although, the structural arc 16 resists bending of the bolus up and down, some flexibility in that direction is possible. This flexibility is important in the use of a guidewire.

The port 18 is open down to the floor 19 of the passage 20 through the bolus 11. In other words, the port 18 does not have side walls.

Referring to FIG. 8, a guidewire 21 is shown placed in the catheter tube 10, so that the tube 10 and bolus 11 are ready for nasogastric insertion. A half loop 22 in the end of the guidewire 21 is seated over bolus 11 and acts as a stylet during insertion of the catheter into the stomach on the guidewire 21.

Figure 12:
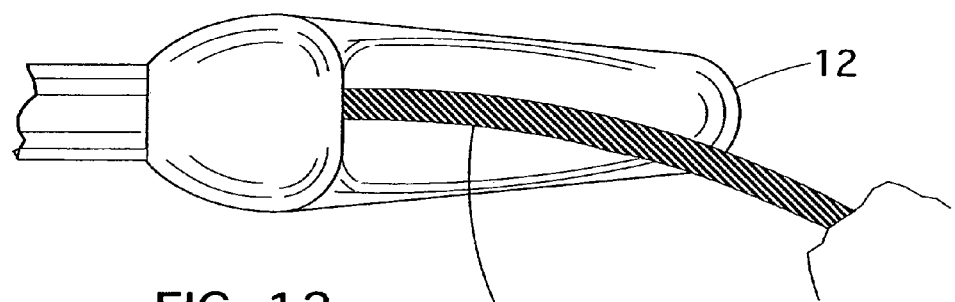
FIG. 12 is a top plan of the jejunal bolus showing the guidewire position when the bolus follows the guidewire around a curve during insertion.

FIGS. 11 and 12 show side and top plan views of the guidewire 21 position when the bolus 11 turns corners during insertion. The bolus tip 12 does not move substantially from the line of the guidewire.

During nasal insertion, it is necessary to position the guidewire so that it remains positioned correctly just behind the tip bolus 11. A flexible plug 23 shown in FIG. 9 is slipped over guidewire 21 by forcing it into slot 24. The guidewire is then positioned in the tube. The plug 23 is forced into a connector (not shown). The plug 23 is compressed by the connector, thereby trapping the guidewire in its correct position in relation to the tip bolus 11.

The jejunal bolus 11 has application in all nasogastric feeding and is an improvement over all tips, including those of the aforementioned patents. The use of the "fat" size bolus in the catheter of the invention is key to a number of advantages. The effective OD of the new bolus 11 is 0.230 inches for all French sizes; for example, an OD of 0.140 inches for an 8FR smooth tip, 0.168 inches for a 10FR smooth tip and 0.188 inches for a 12FR smooth tip.

For the design of the bolus 11, the recessed depth of the port 18 is 0.155 inches for the 8FR and 0.165 inches for a 10FR version. The depth is calculated by adding the radius of the OD of the bolus (always 0.115 inches) and the radius of the internal passage. The effective depth is dramatically larger than in prior art designs and offers more protection against occlusion and clogging. The outflow port 18 is fully protected while at the same time coming closer to an open ended tube for outflow. There are no side walls to collect feeding material.

"The "fat" bolus 11 design (0.230 inches OD) offers additional advantages over other "fat" boluses. Insertion is facilitated because the bolus 11 is tapered from its proximal to distal or nose end 12. The nose end 12 has an OD of approximately 0.150 inches, which is similar to the 0.140 inches tip OD of a smooth 8FR tube. This nose end 12 OD is complimented by the 0.230 inches proximal OD from a safety standpoint, because clinical studies have shown that inadvertent pulmonary insertion is minimized by the use of "fat" boluses. The 0.230 inches proximal OD makes the bolus 11 too large to enter the bronchial tree. These features, combined with the ability to insert the catheter 5 over a guidewire, provide both ease of insertion and insurance against inadvertent pulmonary insertion. Effectively, the bolus presents a small, 8FR smooth bullet nose tip for ease of insertion while incorporating a "fat", trailing, tapered shape that resists entering the pulmonary tree."

The "fat" bolus also aids in the placement and confirmation of placement by flouroscopy. Both the gastric bolus (hereinafter discussed) and the jejunal bolus 11 contain 20% barium and offer thicker, more radiopaque parts to identify port placement in both the stomach and the jejunum.

Referring now to FIGS. 13–29, a gastric/jejunal catheter embodying features of the invention is seen generally at 6. The catheter 6 includes a dual lumen tube 30, a gastric/jejunal bolus 26, a single lumen tube 10 and a jejunal bolus 11.

FIGS. 13 and 14 are side and top plan views of the transitional, gastric/jejunal bolus 26. The bolus 26 is tapered at 29, which is approximately where the section seen in FIG. 16 is taken. A reinforcing structural arc 28 begins at this point and extends under the bolus 26 along its length to prevent bending at the port 27. A dual lumen "D" tube 30 and an 8FR single lumen tube 10 enter the bolus 26 at opposite ends.

The bolus 26 contains a jejunal passage 51 which extends between the nose end 52 and the connector end 53 of the bolus 26 and connects the jejunal lumen 38 in the tube 30 at the connector end 53 and the single lumen 39 in the tube 10 at the nose end 52. The bolus 26 contains a gastric passage 54 which extends between, and connects the port 27 and the gastric lumen 37 in the tube 30.

Referring to FIGS. 15 to 22, the floor 31 of the gastric port 27 in the bolus 26 is shown in FIGS. 15 and 17. The port 27 slopes gradually on both sides to the surface of the septum 42, which forms the "D" shaped jejunal passage 51 below and the "D" shaped gastric passage 54 above. The jejunal passage 51 begins transition at 32 to a full, 8FR size oval at 33 where it is enlarged to form an 8FR size socket 34. The socket 34 is 0.185 inches deep.

In FIG. 17 the floor 31 of the port 27 is seen at the base of gastric passage 54. The floor 31 of the port 27 extends to the edge of the tube at 35. The bolus 26 portion distal to the port 27 has a gradual slope that reaches the same height 36 as the proximal portion of the bolus at 29.

In the dual lumen "D" tube 30, the gastric lumen 37 and the jejunal lumen 38 separated by a septum 44 are identical in size. FIG. 20 shows the cross-sectional area of low for each these lumens. FIG. 22 shows the cross-sectional area of the lumen 39 in the 8FR tube 10. Note that the cross-section area for flow is the same for both the gastric and jejunal lumens 37 and 38, an area of 0.005 in$^2$.

FIGS. 15, 26, 27, 28 and 29 illustrate the method of attaching the "D" tube 30 to the midport bolus 26. The top portion of the end of the "D" tube 30 that will be inserted into the bolus 26 is cut (or ground) off to a level one-half the thickness of the septum 44, forming flap 41. The length of the flap 41 is 0.050 inches. The bolus septum 41 has a molded matching flap 40.

A jig (not shown) that matches the lumen 37 is inserted into the port 27 and it extends out through the end of the bolus 26. The tube 30 is dipped into solvent and is slipped over the extended jig. The tube 30 is then pushed over the jig until it seats itself in the bolus 26. In this fashion, the two flaps 40 and 41 seal in an overlapped position, eliminating any potential for leakage between the two lumens 37 and 38.

Figure 25:
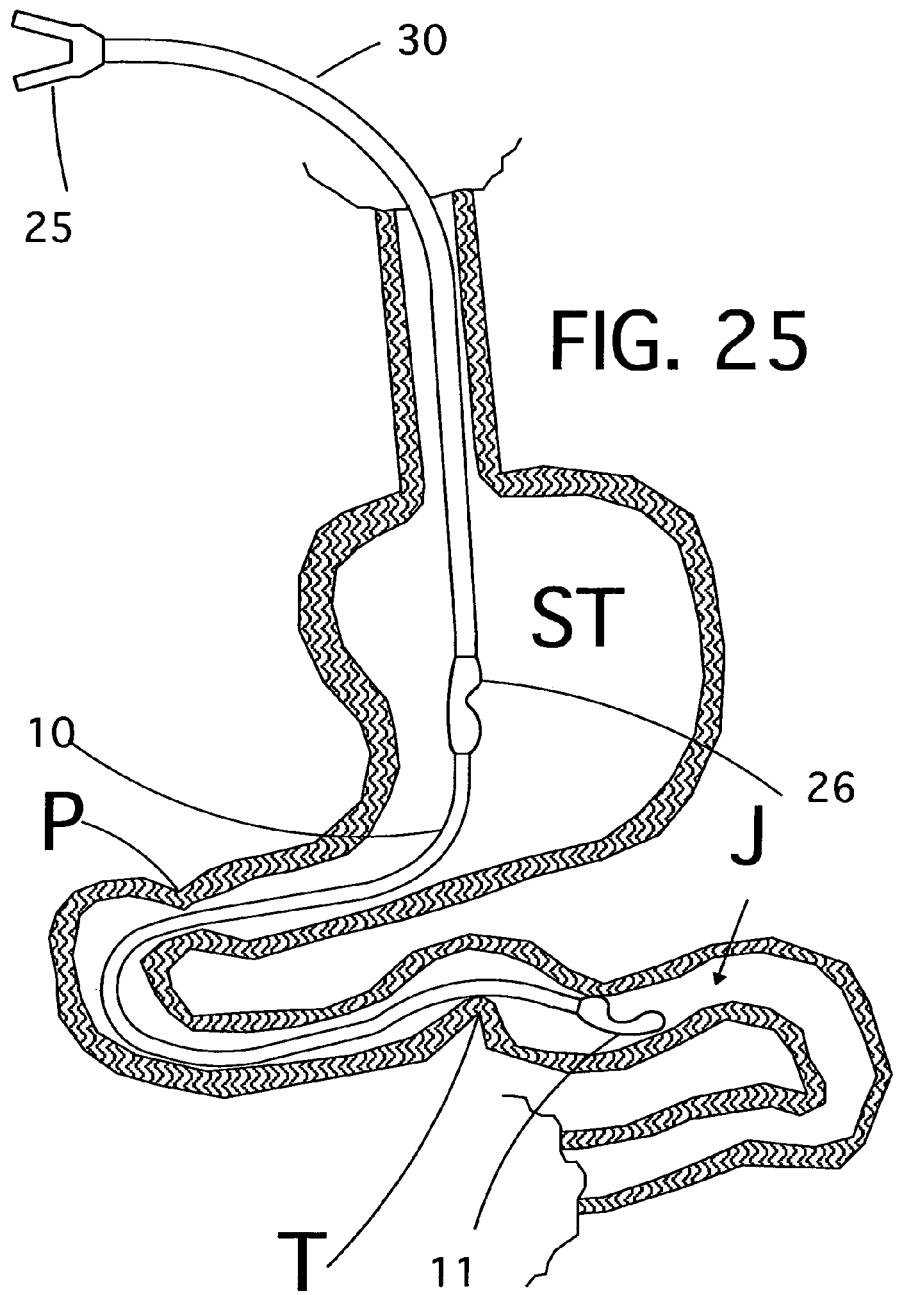
FIG. 25 shows the gastric/jejunal catheter of the invention in place in a stomach and jejunum.
Figure 30:
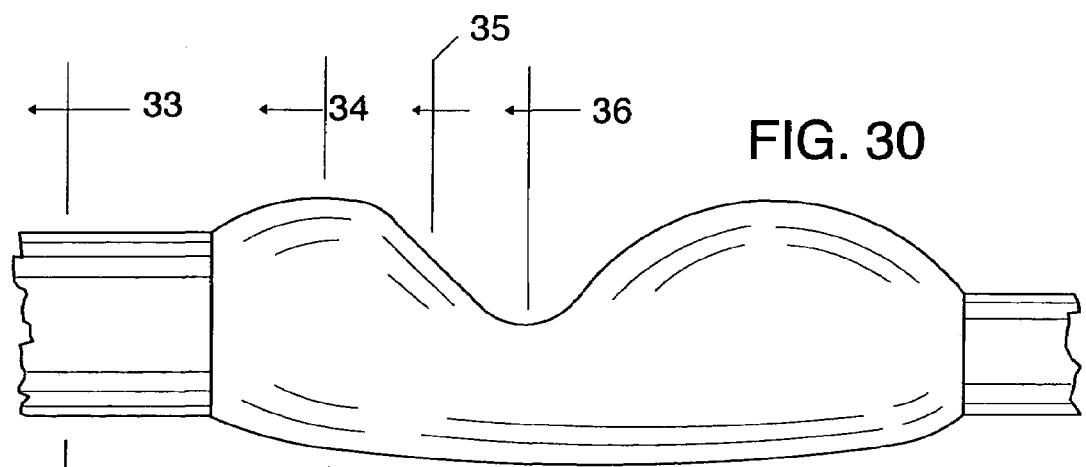
FIG. 30 is a side elevational view of another form of gastric/jejunal catheter.
Figure 37:
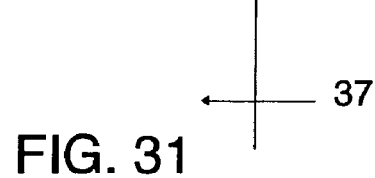
FIG. 37 is a sectional view taken along line 37—37 of FIG. 31.
Figure 31:
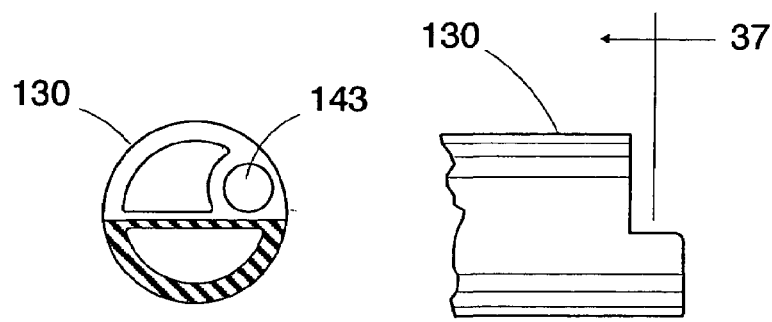
FIG. 31 is a side elevational view of the distal end of the gastric lumen seen in FIG. 30.
Figure 32:
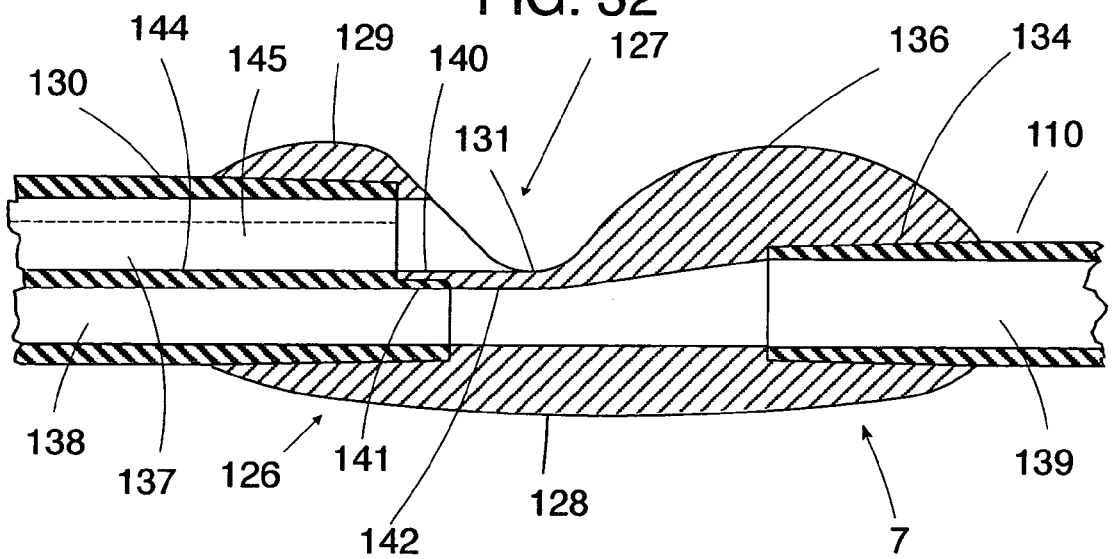
FIG. 32 is a longitudinal section through the catheter of FIG. 30.
Figure 33:
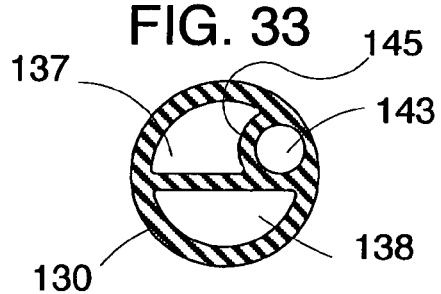
FIG. 33 is a sectional view taken along line 33—33 of FIG. 30.
Figure 34:
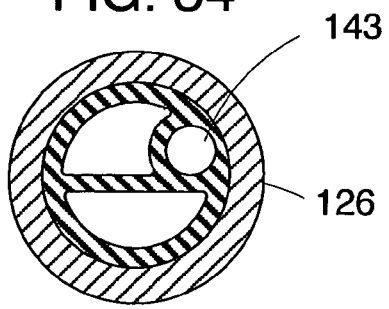
FIG. 34 is a sectional view taken along line 34—34 of FIG. 30.
Figure 35:
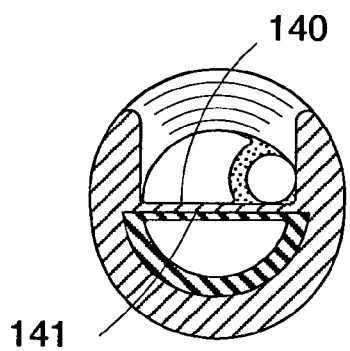
FIG. 35 is a sectional view taken along line 35—35 of FIG. 30.
Figure 36:
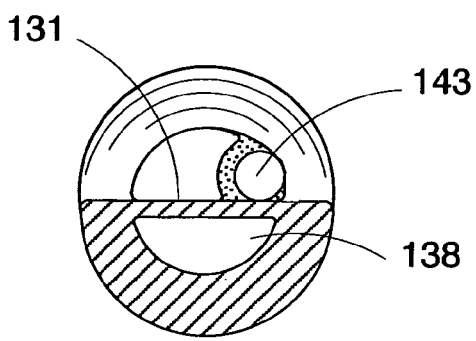
FIG. 36 is a sectional view taken along line 36—36 of FIG. 30.

FIGS. 23 and 24 show the complete catheter 6. FIG. 25 shows the catheter 6 in place. The "D" tube 30 is approximately 36 inches in length. This length assures that the transitional bolus 26 is placed in the stomach, not the intestine. The jejunal 8FR tube 10 is approximately 25 inches long, which assures placement beyond the Ligament of Treitz T. The overall length of the catheter 6 is therefore 60 inches or more when the "Y" connector 25 and the boluses 11 and 26 are included.

The jejunal bolus 11 is 0.684 inches long. The gastric bolus 26 is 0.749 inches long. The 12FR "D" tube 30 has walls that are 0.018 inches thick, the same as the septum 44. A normal 12FR single lumen feeding tube has walls that are 0.029 thick. The tube 30 can have thinner walls because the septum 44 helps support the tube. It is also important that the tube be flexible.

An object with the catheter 6 is to employ the largest tube possible. 8FR tubes have proven to be reliable over long periods of use. The combination of a 12FR "D" tube 30 and a 8FR single lumen tube 10 is the preferred catheter 6. However, other combinations are possible.

Referring now to FIGS. 30–37, another gastric/jejunal catheter embodying features of the invention is seen generally at 7. The catheter 7 includes a triple lumen tube 130, a gastric/jejunal bolus 126, a single lumen jejunal tube 110 and a jejunal bolus 111.

The single lumen jejunal tube 110 and bolus 111 are identical to those hereinbefore described in the catheter 5. Thus, corresponding reference numerals plus 100 digits identify corresponding parts. The catheter 7 is distinguished from the catheter 6 in the construction and use of the triple lumen tube 130.

The method of connecting tube 130 and bolus 126 is similar to that in catheter 6 and is shown in FIGS. 31, 32, 35 and 37. The top of the tube 130, including a portion of third lumen 143 and the septum segment 145 which forms its side is ground down to one-half the level of the "D" septum 144 to form flap 141. The parts are attached in the same manner as catheter 6.

As is the case with catheter 6, both the jejunal lumen 138 and the gastric lumen 137 have cross-sectional areas of 0.005 inches which is equal to an 8FR tube. The gastric lumen 137 and the air lumen 143 both open to port 127.

The proximity of these lumens 137 and 143 to each other at the port 127 is important. Gastric lumen 137 in normal usage is under constant vacuum pressure. As described before, the recessed design of port 127 assures that the gastric lumen 137 will not be occluded. Occlusion is further prevented because the inflow of air to the stomach through lumen 143 is directly adjacent to the gastric port 127 and will always balance the pressure in the stomach. The possibility of the port 127 becoming occluded because it is isolated from the inflow of air is eliminated.

Although there is normally little tendency for fluid to back up into the air lumen 153, it may include a one-way valve in the triple lumen connector arm (not shown) of lumen 153. This valve prevents flow from the stomach into the lumen.

The single lumen and the dual lumen tubes are normally inserted with an internal stylet or over a guidewire. The triple lumen tube is normally placed during surgery by the anesthesiologist and the surgeon. With the patent's belly open, the anesthesiologist advances the tube into the stomach. The surgeon feels through the stomach wall for the shape of the bolus 111 tip and then "milks" the tip out of the stomach until the tip is positioned beyond the Ligament of Treitz T in the jejunum. The surgeon then feels for the transitional bolus 126 in the stomach and positions it in the stomach just outside of the pylorus P, thus assuring that the bolus with its suction capability is at the lowest part of the stomach. The large shape of both the bolus 111 and the bolus 126 assist in identifying the position of the catheter during the insertion.

The invention is described here in the context of NGJ catheters. Principles of the invention may apply equally well to other types of catheters, however, including but not limited to Foley catheters, urethral catheters and catheters for use in such diverse applications as such intravenous, pharyngeal, esophageal, rectocolonic, choledochal gastric, nasal and endobronchial procedures.

What is claimed is:

1. A nasogastric/jejunal catheter comprising:
   a) an elongated, flexible first catheter tube containing first and second lumens extending from a proximal end of the first tube to a distal end thereof;
   b) a first bolus having a connector end connected to said distal end of said first catheter tube, said first bolus having a nose end and containing a first passage and a second passage therein communicating with said first and second lumens, respectively, of said first catheter tube at said connector end of said first bolus;
   c) said first passage extending axially through said first bolus to an opening in said nose end of said first bolus, said second passage extending axially through said first bolus to a port opening radially through a side of said first bolus;
   d) an elongated second catheter tube containing a lumen extending from a proximal end of the second tube to a distal end thereof, said proximal end of said elongated second catheter tube being connected to said nose end of said first bolus so that said second catheter tube lumen is in communication with said first passage in said first bolus;
   e) a second bolus connected to said distal end of said second catheter tube, said second bolus having a nose end and a connector end and containing a passage therein communicating with said lumen in said second catheter tube at said connector end of said second bolus;
   f) said second bolus having a port therein communicating with said passage in said second bolus.

2. The catheter of claim 1 further characterized in that:
a) said second bolus has a generally bullet shaped nose on said nose section;
b) said second bolus port being the only port in said second bolus.
3. The catheter of claim 1 further characterized in that:
a) said second bolus is generally frusto-conical in outside configuration;
b) the maximum outside diameter (OD) of said second bolus being substantially larger than the OD of said second catheter tube.
4. The catheter of claim 1 further characterized in that:
a) said first catheter tube contains a third lumen;
b) said third lumen communicating with said radially opening port in said first bolus.
5. The catheter of claim 4 further characterized in that:
a) said first and second lumens in said first catheter tube are separated by a septum:
b) at least a portion of said third lumen being formed by said septum.
6. The catheter of claim 5 further characterized by and including:
a) a branch segment of said septum also forming a portion of said third lumen.
7. The catheter of claim 1 further characterized by and including:
a) Y-connector mounted on the proximal end of said first catheter tube and containing passages communicating with said first and second lumens, respectively in said first catheter tube.
8. The catheter of claim 1 further characterized in that:
a) said second catheter tube has a predetermined outside diameter (OD); and
b) said second bolus has a maximum OD adjacent said connector end where it joins said second lumen, said maximum OD being at least 25% larger than said predetermined OD.
9. The catheter of claim 8 further characterized in that:
a) said second tube is an 8FR size tube.
10. The catheter of claim 9 further characterized in that:
a) said second and third lumens communicate with said port through said second passage.
11. The catheter of claims 10 further characterized in that:
a) said third lumen has a smaller cross-sectional area than said second lumen.
12. The catheter of claim 1 further characterized in that:
a) said radially opening port in said first bolus is open around the sides of said first bolus substantially down to the base of said second passage in said first bolus.
13. The catheter of claim 1 further characterized in that:
a) said second bolus has a generally bullet shaped nose on said nose end;
b) said second bolus port opening radially of said second bolus.
14. A nasogastric/jejunal catheter comprising:
a) an elongated, flexible first catheter tube having a proximal end and a distal end;
b) an elongated, flexible second catheter tube having a proximal end and a distal end;
c) a generally cylindrical mid-port bolus connecting said distal end of said first catheter tube with said proximal end of said second catheter tube;
d) said first catheter tube containing a feeding lumen and an aspirating lumen;
e) said second catheter tube containing a feeding lumen;
f) said mid-port bolus containing a radially opening port in fluid communication with said aspirating lumen in said first catheter tube and a passage connecting said feeding lumen in said first catheter tube in fluid communication with said feeding lumen in said second catheter tube; and g) a port on the distal end of said second catheter tube;
h) said first catheter tube being long enough to extend from a patient's nose or mouth into the ptatient's stomach and said second catheter tube being long enough to extend from the patient's stomach into the patient's jejunum.
15. The catheter of claim 14 further characterized in that:
a) said port on the distal end of said second catheter tube is formed in a tip bolus attached to said distal end of said second catheter tube; and
b) said tip bolus is generally cylindrical and said port therein opens radially therefrom.
16. The catheter of claim 15 further characterized in that:
a) said tip bolus has a maximum outside diameter which is at least 25 percent larger than the maximum outside diameter of said second catheter tube.
17. The catheter of claim 15 further characterized in that:
a) said tip bolus has an unperforated, bullet-shaped nose thereon.
18. The catheter of claim 17 further characterized in that:
a) said port in said tip bolus extends around more than 180° of the circumference of said tip bolus.
19. The catheter of claim 14 further characterized in that:
a) said second catheter tube is approximately 25 inches long.
20. The catheter of claim 19 further characterized in that:
a) said second catheter tube is approximately 36 inches long.
21. The catheter of claim 20 further characterized in that:
a) said second catheter tube is an 8FR size tube.
22. A catheter for delivering liquid nutrients directly into a patient's intestinal tract, while, at the same time, aspirating the patient's stomach, comprising:
a) a first catheter tube containing first and second lumens extending from a proximal end to a distal end of the tube, said first catheter tube being long enough to extend from outside the patient's nasal passage to inside the patient's stomach;
b) a first bolus having a connector end connected to said distal end of said first catheter tube, said first bolus having a nose end and containing a passage communicating with said first lumen, said passage extending axially through said first bolus to an opening in said nose end of said first bolus;
c) a radially opening port formed at least partially in said first bolus between said nose end and said connector end of said first bolus and communicating with said second lumen;
d) a second catheter tube containing a lumen extending from a proximal end of the second tube to a distal end of second catheter tube, said proximal end of said second catheter tube being connected to said nose end of said first bolus so that said second catheter tube lumen is in communication with said passage in said first bolus, said second catheter tube being long enough to extend from inside the patient's stomach to inside the patient's intestinal tract;
e) a second bolus having a connector end connected to said distal end of said second catheter tube, said second bolus having an nose end and an attachment end;
f) said second bolus having a port opening therefrom and communicating with said lumen in said second catheter.
23. The catheter of claim 22 further characterized in that:
a) said second bolus has a generally bullet shaped nose on said nose end;
b) said second bolus port opening radially of said second bolus.

* * * * *